US00PP21535P2

(12) United States Plant Patent

Grosser et al.

(10) Patent No.: US PP21,535 P2

(45) Date of Patent: Nov. 30, 2010

(54) SWEET ORANGE TREE NAMED 'SF14W-62'

(50) Latin Name: ***Citrus sinensis* L. Osbeck**
Varietal Denomination: SF14W-62

(75) Inventors: Jude W. Grosser, Winter Haven, FL (US); Frederick G. Gmitter, Jr., Lakeland, FL (US); William S. Castle, Lake Alfred, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 12/454,449

(22) Filed: May 18, 2009

(51) Int. Cl.
*A01H 5/00* (2006.01)

(52) U.S. Cl. ..... Plt./202

(58) Field of Classification Search ..... Plt./202
See application file for complete search history.

(56) References Cited

OTHER PUBLICATIONS

Grosser, et al. (2007) Somaclonal Variation in Sweet Orange: Practical Applications for Variety Improvement and Possible Causes In: *Citrus* Genetics, Breeding and Biotechnology (ed. I.A. Khan). CAB International. pp. 219-233.

Larkin, et al. (1981) Somaclonal Variation—a Novel Source of Variability from Cell Cultures for Plant Improvement. Theor. Appl. Genet. 60, pp. 197-214.

*Primary Examiner*—June Hwu
(74) *Attorney, Agent, or Firm*—Jondle & Associates, P.C.

(57) ABSTRACT

A new 'Valencia'-derived sweet orange tree particularly distinguished by producing trees that bear fruit that ripens 4 to 8 weeks earlier than standard 'Valencia' trees, trees that have an upright and moderately vigorous growth habit, trees that have a tendency for terminal fruit bearing and fruit having excellent juice quality, is disclosed.

2 Drawing Sheets

Genus and species: *Citrus sinensis* L. Osbeck.
Variety denomination: 'SF14W-62'.

BACKGROUND OF THE NEW PLANT

The invention relates to a new and distinct variety of sweet orange tree, *Citrus sinensis* L. Osbeck, named 'SF14W-62'. SF14W-62 is a moderately vigorous tree that produces standard 'Valencia' type sweet orange fruit but with a significantly earlier fruit maturation date (4 to 8 weeks) than standard 'Valencia' trees. In Florida, fruit can generally be harvested from mid-January through February, depending on environmental conditions. Juice quality from fruit of 'SF14W-62' is equivalent to that of 'Valencia', the highest quality juice from oranges currently available. 'SF14W-62' provides the processing industry with earlier blending opportunities with 'Hamlin' or 'Midsweet' sweet oranges to improve the flavor and color of NFC (Not From Concentrate) orange juice. In the event of January or February freeze-mandated harvests in Florida, this blending opportunity would allow for grade A juice recovery and would significantly lessen economic losses as would normally be encountered with standard 'Valencia' oranges that have not reached full maturity at this time.

'SF14W-62' originated as a somaclonal tree regenerated from protoplasts isolated from an embryogenic suspension of tissue culture of standard 'Valencia' (*Citrus sinensis* L. Osbeck) in 1989. For the methodology, see Grosser, J.W. and F.G.J. Gmitter (1990). Protoplast fusion and citrus improvement. pp. 339-374. In: Janick, J. (Ed.). *Plant Breeding Reviews*. Timber Press, Inc, Portland, Oreg., USA. The original 'SF14W-62' tree was grafted to 'Carrizo' (unpatented) citrange rootstock and planted at a collaborative research block in Venus, Fla. in 1991. 'SF14W-62' is a true 'Valencia' sweet orange with an altered maturity date that allows for harvest 4 to 8 weeks earlier than traditional 'Valencia' clones. 'SF14W-62' has been subsequently asexually reproduced by inverted "T" bud-grafting onto widely-used commercial citrus rootstocks 'Carrizo' citrange and 'Swingle' citrumelo. The present invention has been found to retain its distinctive characteristics through successive asexual propagations via an inverted "T" graft.

Plant Breeder's Rights for this cultivar have not been applied for. 'SF14W-62' has not been made publicly available or sold more than one year prior to the filing of this application.

SUMMARY OF THE INVENTION

'SF14W-62' is a new and distinct variety of sweet orange tree which bears fruit that ripens from mid-January through February in central Florida. The trees usually bloom between early to late March in central Florida, depending on seasonal weather. 'SF14W-62' trees are upright and of moderate vigor, with a tendency for alternate bearing. Second and third generation trees are more thorny than traditional 'Valencia' selections, especially on internal scaffold branches; however, thorniness diminishes over time and is less obvious with each generation of propagation. Thorns can be long, but are quite variable. Trees tend to bear more terminal fruit, which can cause long scaffold branches to bend over from the weight of the fruit, but also minimizes the impact of the thorns on harvesting.

'SF14W-62' trees bear fruit that is typical of 'Valencia' trees but 'SF14W-62' fruit ripens 4 to 8 weeks earlier than standard 'Valencia' clones based on the brix/acid ratio (see Table 1). Juice quality of 'SF14W-62' is typical of 'Valencia' in sugar and acid content, color and flavor. The fruit of 'SF14W-62' are juicy and difficult to peel. The fruit of 'SF14W-62' is slightly less seedy than standard 'Valencia' but not seedless. Replicated trials (both $2^{nd}$ generation and top-worked $3^{rd}$ generation trees) to determine yield were destroyed by the Florida state-run canker eradication program. The original tree in Venus, Fla. yielded more than 10 boxes (approximately 90 pounds fruit per box) of fruit in the last year before being destroyed. The cultivar of the present invention appears to be at least as productive in fruit-bearing as standard 'Valencia' trees.

The following are the most outstanding and distinguishing characteristics of this new cultivar when grown under normal horticultural practices in Florida.

1. Trees that bear fruit that ripens 4 to 8 weeks earlier than standard 'Valencia' trees;
2. Trees that have an upright and moderately vigorous growth habit.
3. Trees that have a tendency for terminal fruit bearing; and
3. Fruit having excellent juice quality.

DESCRIPTION OF THE PHOTOGRAPHS

This new sweet orange plant is illustrated by the accompanying photographs which show the plant's form, foliage and fruit. The colors shown are as true as can be reasonably obtained by conventional photographic procedures. The photographs were taken in January 2009.

DESCRIPTION OF THE NEW CULTIVAR

Figure 1:
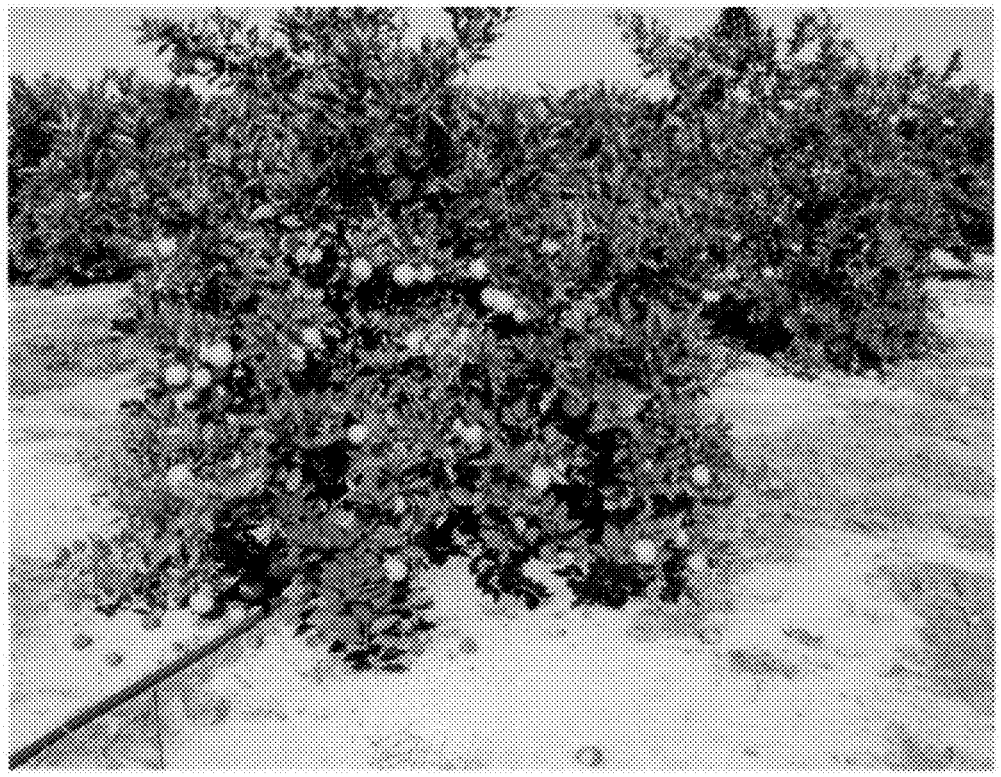
FIG. 1 shows the typical morphology of a 5-year old tree on 'Swingle' citrumelo rootstock, with typical overall plant habit including foliage and fruit.
Figure 2:
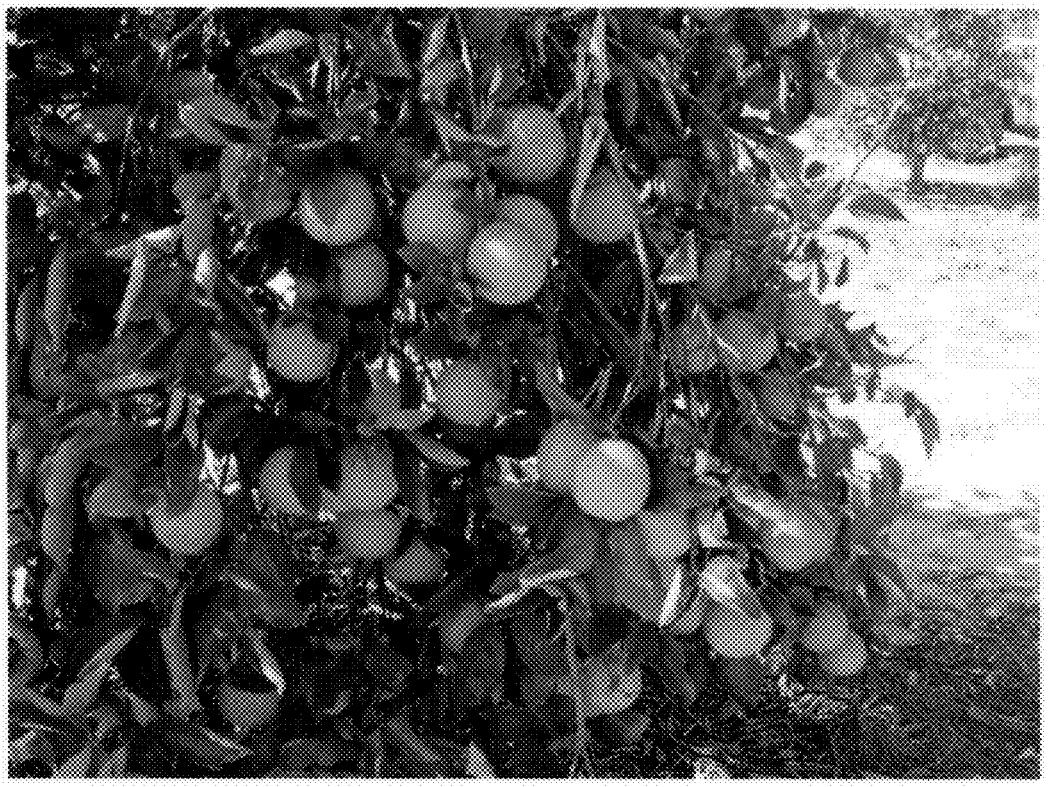
FIG. 2 shows heavy cropping on 7-year old reset tree on rough lemon rootstock, demonstrating cropping capacity.
Figure 3:
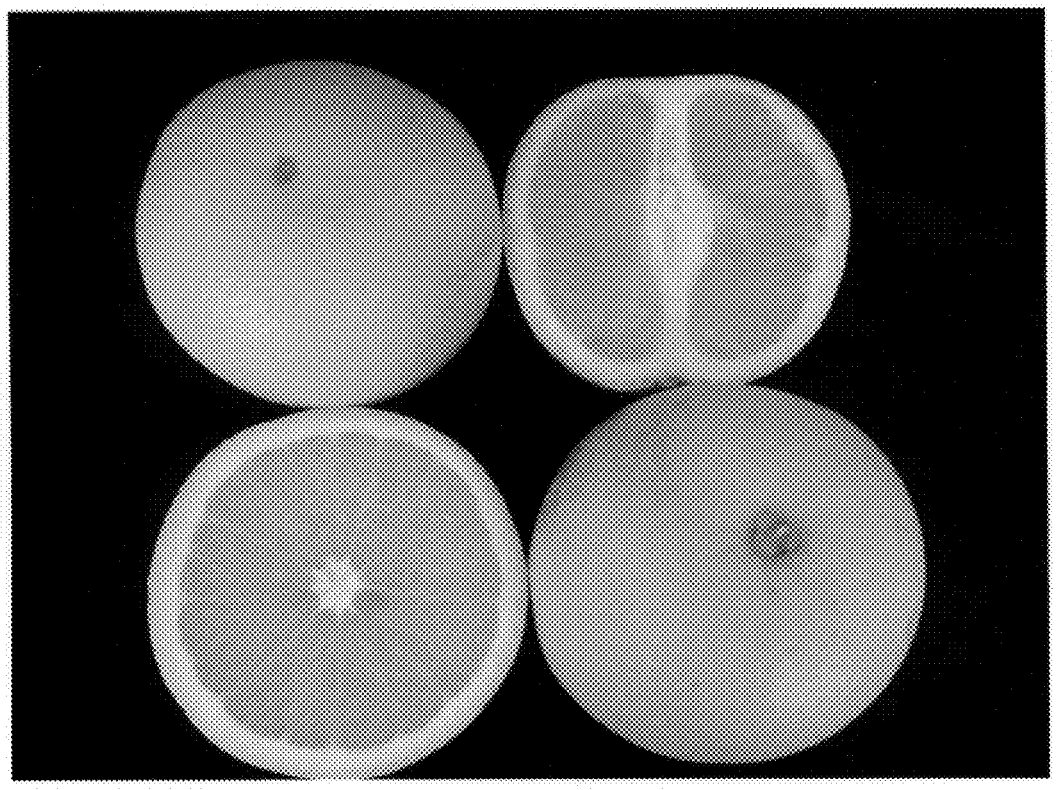
FIG. 3 shows a close-up of the mature fruit, a cross-sectional view and a longitudinal sectional view of the fruit when cut in the center.
Figure 4:
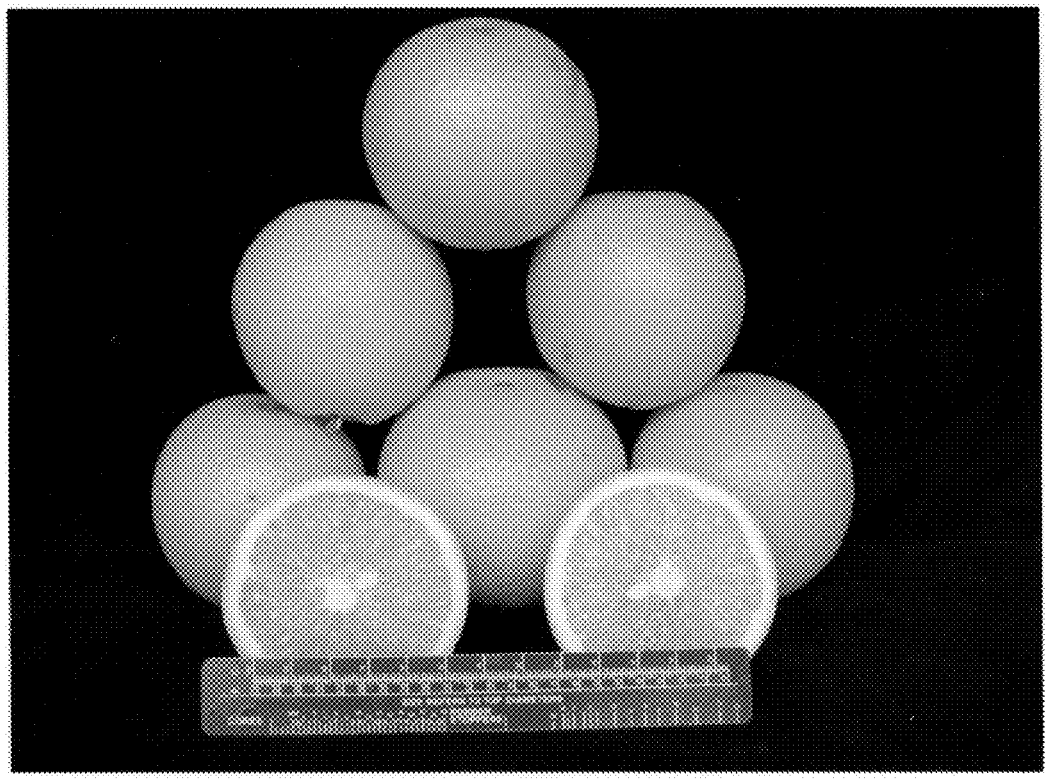
FIG. 4 shows average fruit size and appearance.

The following detailed description defines the characteristics of 'SF14W-62'. The present botanical description was taken from 4 to 5 year-old trees grown on 'Carrizo' rootstock in Lake Alfred, Fla. in 2007 and 2008. The colors (except those in common terms) are described from The R.H.S. Colour Chart published by The Royal Horticultural Society in London, in association with the Flower Council of Holland (2001).

DETAILED BOTANICAL DESCRIPTION

Classification:

*Botanical.*—*Citrus sinensis* L. Osbeck.

*Common name.*—Sweet orange.

*Parentage.*—Somaclonal tree regenerated from protoplasts isolated from an embryogenic suspension of tissue culture of standard 'Valencia' (unpatented).

Tree:

*Ploidy.*—Diploid.

*Form.*—Trees are leggy at first with upright branches, with occasional long branches but eventually become obloid with maturity.

*Vigor.*—Moderate, typical of sweet orange.

*Size* (*average size for* 6 year old tree on Swingle citrumelo rootstock): Width across row: 289.0 cm. Width down row: 276.0 cm. Height: 274.0 cm. Trunk diameter (taken 15.24 cm above the bud/graft union): 9.42 cm.

*Bark color.*—Between RHS 199 (Greyed-brown) to RHS N199A (Greyed-brown).

*Density.*—Canopies are leggy for first few years and become more dense over time.

*Thorn length.*—1.9 cm±1.0 cm.

*Thorn color.*—Same as bark color, between RHS 199 (Greyed-brown) to RHS N199A (Greyed-brown), depending on the age of the bark.

*Thorn shape.*—Straight, lanceolate.

Leaves:

*Type and shape.*—Simple, elliptical.

*Apex.*—Acuminate.

*Base.*—Obtuse.

*Margin.*—Weakly dentate.

*Length.*—8.4 cm±1.6 cm.

*Width.*—4.6 cm±1.2 cm.

*Adaxial color.*—RHS 137B (Green).

*Abaxial color.*—RHS 146D (Yellow-green).

*Texture* (*both surfaces*).—Smooth (not pubescent).

*Petiole.*—Appearance and attachment: Narrow and brevipetiolate. Length: 1.39 cm±0.43 cm. Width: 0.34 cm±0.08 cm. Color: RHS 137B (Green). Wings: Size (average): Length: 2.5 mm. Width: 7.0 mm. Color: RHS 137B.

Flowers:

*Type.*—Hermaphroditic.

*Date of first bloom* (*in central Florida*).—Between late February and mid-March.

*Size* (*average*).—Length: 16.4 mm. Depth: 7.0 mm.

*Calyx size.*—Small.

*Petals.*—Quantity (per flower): 4.4±0.7. Length: 1.52 cm±0.14 cm. Width: 0.63 cm±0.12 cm. Color: RHS 155B (White).

*Sepal.*—Number per flower: 4.2 Size: Length: 4.3 mm. Width: 4.4 mm. Color: RHS 149C.

*Pedicel.*—Length (average): 8.5 mm. Color: RHS 144C.

*Fragrance.*—Typical of 'Valencia' sweet orange.

Fruit:

*Time of maturity.*—Early to late March in central Florida.

*Date of first picking* (*in central Florida*).—Mid January.

*Date of last picking* (*in central Florida*).—Early April.

*General.*—Fruit size is heavily influenced by rootstock type and crop load. Over-cropping leads to smaller fruit, as is typical with sweet orange trees.

*Fruit areola diameter.*—None observed.

*Fruit areola type.*—None observed.

*Shape.*—Spheroid to oblate (fewer oblate fruit than standard 'Valencia').

*Apex.*—Rounded.

*Base.*—truncate.

*Fruit* (*flesh*) *color.*—RHS N25C (Orange).

*Height.*—7.1 cm±3.9 cm for an average crop and 6.3 cm±3.0 cm for a heavy crop.

*Width.*—6.8 cm±3.0 cm for an average crop and 6.4 cm±3.0 cm for a heavy crop.

*Fruit height to width ratio.*—1.04 for an average crop and 0.98 for a heavy crop.

*Fruit weight.*—178.3 g±19.8 g for an average crop and 139.0 g±19.3 g for a heavy crop.

*Fruit core diameter.*—0.9 mm.

*Surface oil glands size.*—Length: Approximately 1.0 mm. Width: Approximately 1.0 mm.

*Fruit rudimentary segments.*—None observed.

*Rind.*—Texture: Pitted. Color: RHS N25C (Orange). Thickness: 0.42 cm±0.04 cm to 0.52 cm±0.09 cm for an average crop and 0.43 cm±0.02 cm for a heavy crop.

*Adherence of mesocarp to endocarp.*—Strong.

*Attachment to stalk* (*strength*).—Medium.

*Albedo color.*—RHS 10D (Yellow).

*Albedo thickness.*—0.2 cm to 0.4 cm.

*Segments.*—Quantity (per fruit): 9.6±0.7 to 10.6±1.0 for an average crop and 10.2±0.6 for a heavy crop. Fruit segment size: Length (average): 7.2 cm. Width (average): 2.7 mm. Wall thickness: Thin. Vesicle thickness: Medium. Vesicle diameter: 0.43 cm.

*Cross-sectional shape of axis.*—Round.

*Pulp color.*—RHS N25C (Orange).

*Fruit axis.*—Semi-hollow.

*Naval.*—Absent.

Seeds:

*Quantity per fruit.*—2.2±1.8 to 2.4±1.8 ('Valencia' has approximately 3.9) for an average crop and 2.7±0.9 for a heavy crop.

*Surface appearance.*—Wrinkled.

*Size (average).*—Length: 1.7 mm. Width: 0.8 mm.

*Seed coat color.*—RHS 158B (Yellow-white).

*Inner seed color.*—RHS 165C (Greyed-orange).

*Outer seed coat color.*—RHS 161D (Greyed-yellow).

*Chalazal end color.*—RHS 165A (Greyed-orange).

*Cotyledon color.*—RHS 157D (Green-white).

Reproductive organs:

*Anthers.*—Shorter than the petals.

*Anther size.*—Length: 2.3 mm. Width: 0.8 mm.

*Anther color.*—RHS 10A (Yellow).

*Stamen quantity (per flower).*—23.9±2.4.

*Stamen (quantity per petal).*—5.5.

*Stamen length.*—13.8 mm.

*Style size.*—Length: 7.5 mm. Diameter: 1.4 mm.

*Pollen color.*—RHS 14A.

Juice data: 'SF14-62W' has a maturity date very comparable to that of 'Midsweet' (unpatented) which is the currently preferred mid-season processing sweet orange cultivar in Florida. 'SF14-62W' has a significantly better juice color than 'Midsweet' and was favored over 'Midsweet' in sensory testing panel tests. Consequently, 'SF14-62W' has excellent potential as a mid-season variety which could be especially useful for blending with low-colored juice from 'Hamlin', for example.

COMPARISON WITH PARENTAL AND KNOWN CULTIVARS

'SF14W-62' differs from the commercial comparison variety 'Alvarina' (U.S. Plant Pat. No. 19,575) in that 'SF14W-62' has darker orange fruit flesh (RHS N25C) than 'Alvarina' (RHS 28C).

Table 1 shows comparative data of juice characteristics from 'SF14W-62' as compared to the parental variety 'Valencia' (unpatented) and Florida industry mid-season cultivars, 'Midsweet' (unpatented) and 'Vernia' (unpatented).

TABLE 1

Juice Data from 'SF14W-62'

| Date | Cultivar | Brix | Acid | Ratio | lb solids | Color |
|---|---|---|---|---|---|---|
| First Generation Tree (Original, location: Venus, Florida, Southern Farms Ltd., 'Carrizo' rootstock) | | | | | | |
| Jan. 28, 2000 | 'SF14W-62' | 11.0 | 0.75 | 14.7 | 4.85 | 38.0 |
| | 'Valencia' | 10.1 | 0.94 | 10.8 | 5.87 | 37.6 |
| Feb. 6, 2001 | 'SF14W-62' | 12.8 | 0.81 | 15.8 | 7.04 | 38.0 |
| | 'Valencia' | 11.7 | 1.00 | 10.3 | 5.88 | 37.5 |
| Jan. 15, 2002 | 'SF14W-62' | 11.8 | 0.86 | 13.8 | n.d. | 37.6 |
| | 'Midsweet' | 12.0 | 0.90 | 13.4 | n.d. | 36.4 |
| Feb. 6, 2003 | 'SF14W-62' | 10.7 | 0.64 | 16.7 | 5.38 | 37.6 |
| | 'Valencia' | 11.7 | 0.97 | 12.0 | 6.15 | 37.9 |
| Jan. 16, 2004 | 'SF14W-62' | 11.8 | 0.77 | 15.3 | n.d. | 38.7 |
| | 'Valencia' | 11.1 | 1.10 | 9.7 | n.d. | 38.0 |
| Second Generation Trees - Alligator Grove, east of St. Cloud, Florida) (Control trees - mature budwood) | | | | | | |
| Jan. 26, 2006 | 'SF14W-62' | 10.6 | 0.84 | 12.6 | n.d. | 39.1 |
| | 'Vernia' | 13.4 | 1.00 | 13.6 | n.d. | 38.5 |
| | 'Midsweet' | 13.2 | 1.13 | 11.9 | n.d. | 37.7 |
| Jan. 23, 2007 | 'SF14W-62' | 10.9 | 0.76 | 14.3 | n.d. | 39.2 |
| | 'Verna' | 11.3 | 0.67 | 17.1 | n.d. | 39.5 |
| Apr. 11, 2007 | 'SF14W-62' | 12.6 | 0.57 | 22.0 | 6.19 | 39.0 |
| | 'Valencia' | 14.1 | 0.83 | 17.0 | 7.76 | 39.8 |
| Jan. 17, 2008 | 'SF14W-62' | 11.1 | 0.76 | 14.6 | 5.90 | 38.2 |
| | 'Vernia' | 12.4 | 0.97 | 12.8 | 6.40 | 38.5 |
| Feb. 25, 2008 | 'SF14W-62' | 10.8 | 0.70 | 15.6 | n.d. | 40.9 |
| | 'Verna' | 11.0 | 0.64 | 17.4 | n.d. | 40.3 |
| | 'Valencia' | 11.7 | 1.4 | 8.6 | n.d. | 38.5 |
| Jan. 14, 2009 | 'SF14W-62' | 10.9 | 0.81 | 13.6 | 5.68 | 38.2 |
| | 'Valencia' | 11.1 | 1.14 | 9.7 | 5.88 | 37.5 |

Juice quality data was obtained from the UF/CREC State Test House

Brix: Is the percent of sucrose determined by a hydrometer

Acid: Is the percent of citric acid determined by standard titration

Ratio: Is the ration of Brix/Acid

Lb solids: Is calculated as pounds of soluble sugars per 90 pound box of fruit.

Color: FDA legal juice color was measured using a Gretag Macbeth color-Eye 3100 spectrophotometer using ProPalette computer software, version 5.2.1 Quality Control 2001.

n.d = not determined

Resistance to insects, disease or pests: Typical of 'Valencia' sweet orange trees.

We claim:

1. A new and distinct cultivar of sweet orange tree as shown and described herein.

* * * * *